(12) United States Patent
Schwab et al.

(10) Patent No.: US 10,610,277 B2
(45) Date of Patent: Apr. 7, 2020

(54) SURGICAL ROD BENDER

(71) Applicant: K2M, Inc., Leesburg, VA (US)

(72) Inventors: Frank Schwab, New York, NY (US); Timmon Ark, Falls Church, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 15/475,253

(22) Filed: Mar. 31, 2017

(65) Prior Publication Data

US 2017/0281252 A1 Oct. 5, 2017

Related U.S. Application Data

(60) Provisional application No. 62/315,914, filed on Mar. 31, 2016.

(51) Int. Cl.
*A61B 17/70* (2006.01)
*A61B 17/88* (2006.01)
*A61B 17/58* (2006.01)

(52) U.S. Cl.
CPC .......... *A61B 17/8863* (2013.01); *A61B 17/58* (2013.01)

(58) Field of Classification Search
CPC .............. A61B 17/8863; A61B 17/7074–7092
See application file for complete search history.

(56) References Cited

U.S. PATENT DOCUMENTS

| | | | | |
|---|---|---|---|---|
| 4,474,046 A * | 10/1984 | Cook | ................. | A61B 17/8863 72/409.16 |
| 5,389,099 A * | 2/1995 | Hartmeister | ....... | A61B 17/8863 606/101 |
| 5,390,521 A * | 2/1995 | Kerze | ................. | B21D 19/005 72/122 |
| 5,490,409 A * | 2/1996 | Weber | ................ | A61B 17/8863 140/106 |
| 5,548,985 A | 8/1996 | Yapp | | |
| 5,564,302 A * | 10/1996 | Watrous | ............. | A61B 17/8863 72/458 |
| 7,488,331 B2 * | 2/2009 | Abdelgany | ........ | A61B 17/8863 606/109 |

(Continued)

OTHER PUBLICATIONS

"Hinge." Merriam-Webster.com. Merriam-Webster, n.d. Web. Nov. 26, 2018. (Year: 2018).*

*Primary Examiner* — Nicholas J Plionis
*Assistant Examiner* — Steven J Cotroneo
(74) *Attorney, Agent, or Firm* — Lerner, David, Littenberg, Krumholz & Mentlik, LLP

(57) ABSTRACT

A rod bender for bending a surgical rod includes first and second arms. The first arm includes first and second engaging portions. The second arm includes third and fourth engaging portions. The rod bender is reconfigurable between a first configuration in which the second and fourth engaging portions of the respective first and second arms engage the surgical rod such that spreading of the first and third engaging portions of the respective first and second arms bends the surgical rod in a first orientation and a second configuration in which the first engaging portion of the first arm and the fourth engaging portion of the second arm engage the surgical rod such that spreading of the second engaging portion of the first arm and the third engaging portion of the second arm bends the surgical rod in a second orientation opposite to the first orientation.

22 Claims, 6 Drawing Sheets

(56) References Cited

U.S. PATENT DOCUMENTS

| | | | |
|---|---|---|---|
| 8,337,506 B2 * | 12/2012 | Cunliffe | A61B 17/7004 606/101 |
| 8,459,090 B2 * | 6/2013 | Wilcox | B21F 1/002 140/106 |
| 8,506,603 B2 | 8/2013 | McClintock et al. | |
| 8,551,107 B2 * | 10/2013 | Ng | A61B 17/1728 606/101 |
| 8,607,603 B2 * | 12/2013 | Justis | A61B 17/8863 140/123 |
| 8,714,427 B2 | 5/2014 | McClintock et al. | |
| 9,095,378 B2 | 8/2015 | Wallenstein | |
| 9,114,447 B2 | 8/2015 | Yamamoto | |
| 9,186,182 B2 | 11/2015 | Wallenstein | |
| 9,295,494 B2 | 3/2016 | Strauss et al. | |
| 9,421,038 B2 | 8/2016 | Noordeen et al. | |
| 9,956,599 B2 * | 5/2018 | Tellman | A61B 17/8863 |
| 2011/0264100 A1 * | 10/2011 | Sixto, Jr. | A61B 17/8863 606/101 |
| 2015/0289918 A1 * | 10/2015 | Burckhardt | A61B 17/8863 264/339 |

\* cited by examiner

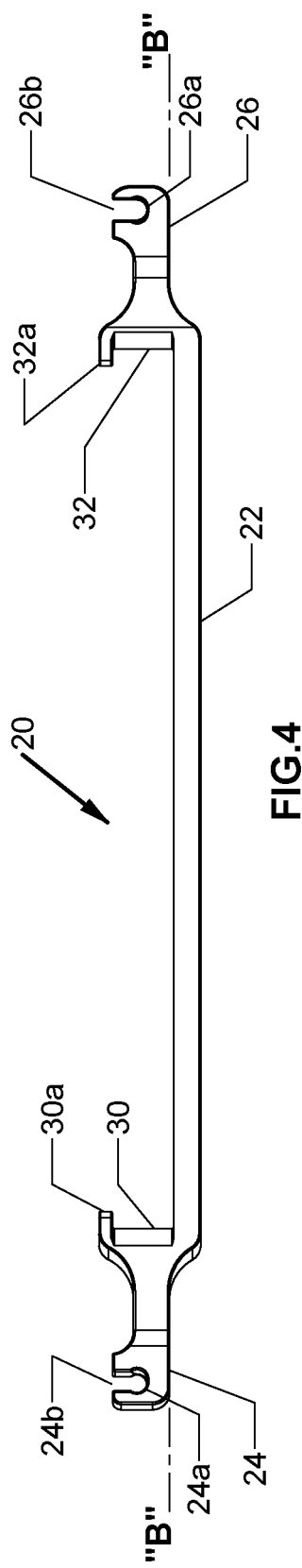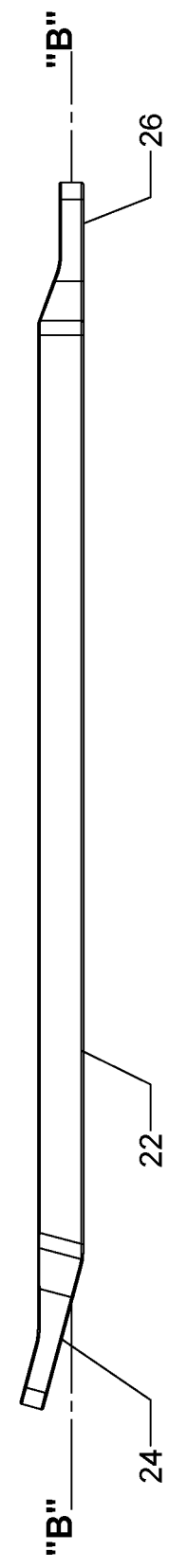

SURGICAL ROD BENDER

CROSS-REFERENCE TO RELATED APPLICATION

This application claims priority to, and the benefit of, U.S. Provisional Patent Application Ser. No. 62/315,914, filed on Mar. 31, 2016, the entire contents of which is incorporated by reference herein.

BACKGROUND

Technical Field

The present disclosure relates to a surgical instrument, and more particularly, to a rod bender.

Background of Related Art

The spine is a flexible structure capable of a large range of motion. There are various disorders, diseases, and types of injury, which restrict the range of motion of the spine or interfere with important elements of the nervous system. The problems include scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages, and cadaver and human bone implants. In order to facilitate stabilizing the spine and keeping the interbody in position, other implants are commonly employed, such as surgical rods. Surgical rods are typically made of cobalt chrome, stainless steel, or titanium alloy. However, in order to transition to a less stiff construct at the top, other less rigid materials and rod shapes may be employed to provide the desired stiffness.

Therefore, there is a continuing need for a rod bender that can create varying severities or contours of bend in a surgical rod to meet the needs of each patient, while expediting the surgical process.

SUMMARY

In accordance with an embodiment of the present disclosure, there is provided a rod bender for bending a surgical rod. The rod bender includes first and second arms. The first arm defines a longitudinal axis and includes first and second engaging portions configured to engage the surgical rod. At least one of the first or second engaging portions defines an acute angle with respect to the longitudinal axis. The second arm includes third and fourth engaging portions configured to engage the surgical rod. The rod bender is reconfigurable between a first configuration in which the second and fourth engaging portions of the first and second arms engage the surgical rod such that spreading of the first and third engaging portions of the first and second arms bends the surgical rod in a first orientation and a second configuration in which the first engaging portion of the first arm and the fourth engaging portion of the second arm engage the surgical rod such that spreading of the second engaging portion of the first arm and the third engaging portion of the second arm bends the surgical rod in a second orientation opposite to the first orientation.

In an embodiment, each engaging portion of the first and second arm may define a notch configured to receive the surgical rod and an opening leading into the notch. In particular, the openings of the first and second engaging portions of the first arm may be transverse to the longitudinal axis of the first arm. In addition, the openings of the first and second engaging portions of the first arm may be defined in opposite directions.

In another embodiment, at least one of the third or fourth engaging portions of the second arm may define an acute angle with respect to a longitudinal axis defined by the second arm. In addition, the third engaging portion of the second arm may define the acute angle with respect to the longitudinal axis of the second arm. Furthermore, the first engaging portion of the first arm may define the acute angle with respect to the longitudinal axis of the first arm.

In an embodiment, the second arm may include a hinge portion adjacent the third or fourth engaging portions. The first arm may be configured to hinge against the hinge portion of the second arm.

In an embodiment, the second arm may include an elongate body extending between the third and fourth engaging portions of the second arm. The elongate body may be aligned with the longitudinal axis of the second arm.

In accordance with another embodiment of the present disclosure, there is provided a rod bender for bending a surgical rod. The rod bender includes first and second arms. The first arm includes opposing first and second ends. The second arm includes opposing third and fourth ends. The rod bender is selectively configurable between a first configuration in which the second and fourth ends of the respective first and second arms engage the surgical rod for bending the surgical rod in a first orientation and a second configuration in which the first end of the first arm and the fourth end of the second arm engage the surgical rod for bending the surgical rod in a second orientation opposite to the first orientation.

In an embodiment, the surgical rod in the first orientation may define a convex profile. In another embodiment, the surgical rod in the second orientation may define a concave profile.

In accordance with another aspect of the present disclosure, there is provided a method of surgery. The method includes providing a rod bender including a first arm including first and second engaging portions configured to engage a surgical rod and a second arm including third and fourth engaging portions configured to engage the surgical rod. The first engaging portion is offset from a longitudinal axis defined by the first arm. The method further includes securing a surgical rod with the second and fourth engaging portions or the first and fourth engaging portions of the respective first and second arms. The method further includes bending the surgical rod by spreading the first and third engaging portions or the second and third engaging portions of the respective first and second arms.

In an embodiment, securing the surgical rod may include engaging the surgical rod with the second engaging portion of the first arm and the fourth engaging portion of the second arms such that spreading of the first engaging portion of the first arm and the third engaging portion of the second arm bends the surgical rod in a convex profile.

In another embodiment, securing the surgical rod may include engaging the surgical rod with the first engaging portion of the first arm and the fourth engaging portion of the second arm such that spreading of the second engaging portion of the first arm and the third engaging portion of the second arm bends the surgical rod in a concave profile.

BRIEF DESCRIPTION OF THE DRAWINGS

The above and other aspects and features of the present disclosure will become more apparent in light of the following detailed description when taken in conjunction with the accompanying drawings in which:

FIG. 4 is a top view of a second lever arm of the rod bender of FIG. 1;

FIG. 5 is a side view of the second lever arm of FIG. 4;

DETAILED DESCRIPTION

Figure 1:
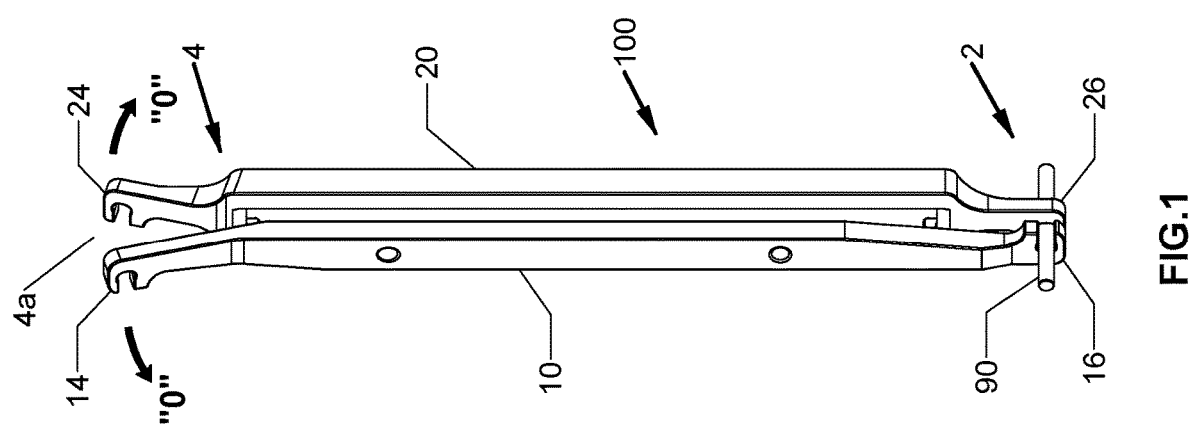
FIG. 1 is a perspective view of a rod bender in accordance with an embodiment of the present disclosure illustrating a first configuration of the rod bender.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during use as will be described hereinbelow. In addition, the term "cephalad" is used in this application to indicate a direction toward a patient's head, whereas the term "caudad" indicates a direction toward the patient's feet. Further still, the term "medial" indicates a direction toward the middle of the body of the patient, while the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

With reference to FIG. 1, an embodiment of the present disclosure is shown generally as a rod bender 100 selectively configurable to create varying severities or contours of bend in a surgical rod 90. For example, rod bender 100 in a first configuration (FIG. 1) may create a convex bend in surgical rod 90, and rod bender 100 in a second configuration (FIG. 7) may create a concave bend in surgical rod 90. Rod bender 100 may be utilized prior to fixating surgical rod 90 in a patient, i.e., surgical rod 90 may be bent, e.g., prior, to being inserted in the patient, or in-situ. Rod bender 100 may be made of titanium, titanium alloy, stainless steel, cobalt chrome, a combination thereof, or any other suitable biocompatible material. Surgical rod 90 is utilized to secure vertebral bodies and/or an intervertebral cage interposed between adjacent vertebral bodies to promote spinal fusion. Reference may be made to U.S. Pat. No. 9,295,494, filed on Nov. 8, 2012, entitled "Spinal Stabilization System," the entire content of which is incorporated herein by reference, for a detailed discussion of the construction and operation of a surgical rod.

Figure 7:
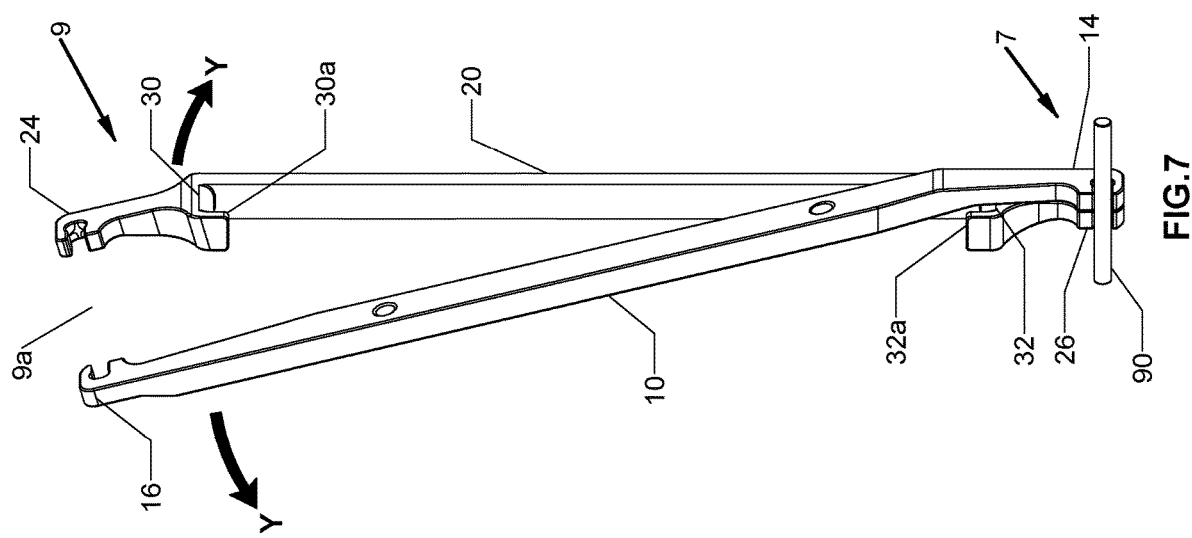
FIG. 7 is a perspective view of the rod bender of FIG. 1 illustrating a second configuration of the rod bender.

With reference to FIGS. 1 and 7, rod bender 100 includes first and second lever arms 10, 20. First and second lever arms 10, 20 are selectively mated to create varying severities or contours of bend such as, e.g., a convex bend (FIG. 1) or a concave bend (FIG. 7), in surgical rod 90. Rod bender 100 in the first configuration (FIG. 1) includes an engaging end 2 and a non-engaging end 4. Rod bender 100 in the second configuration (FIG. 7) includes an engaging end 7 and a non-engaging end 9.

Figure 2:
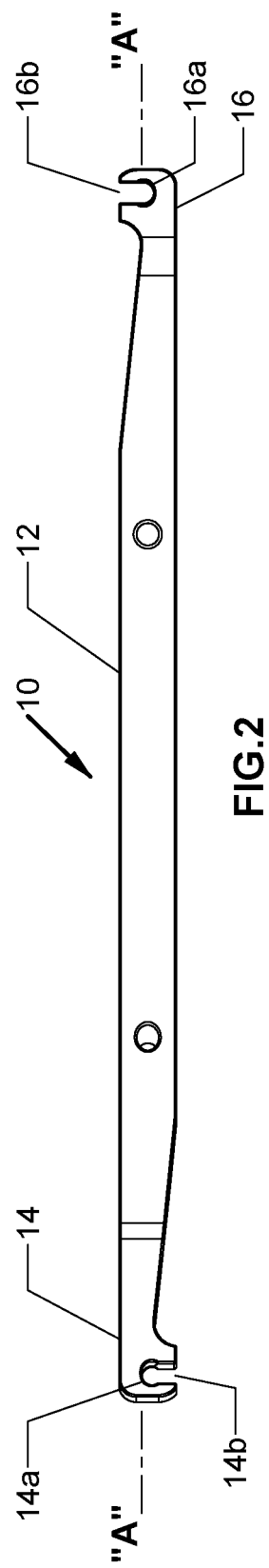
FIG. 2 is a top view of a first lever arm of the rod bender of FIG. 1.
Figure 3:
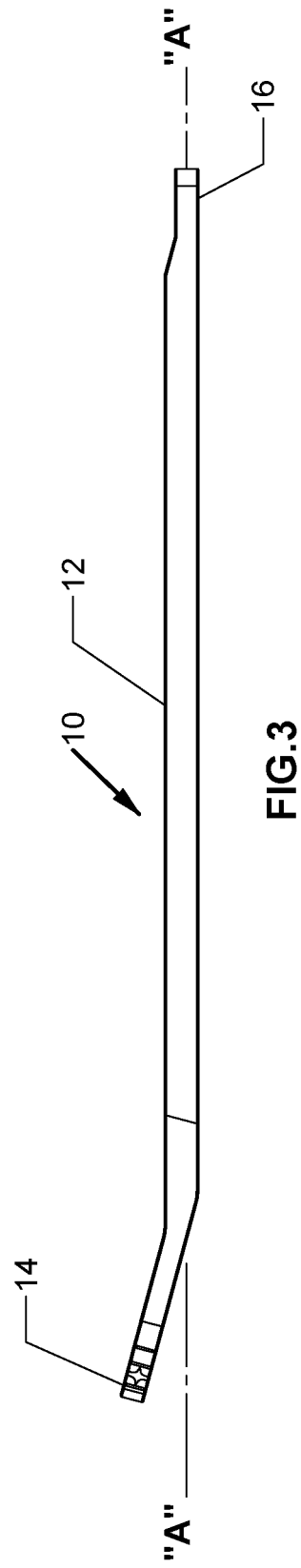
FIG. 3 is a side view of the first lever arm of FIG. 2.

With reference now to FIGS. 1-3, first lever arm 10 includes an elongated body 12 extending between first and second engaging portions 14, 16. Each of first and second engaging portions 14, 16 defines a notch 14a, 16a dimensioned to receive surgical rod 90 therein. Each of first and second engaging portion 14, 16 further defines an opening 14b, 16b leading into notch 14a, 16a. Openings 14b, 16b may be transverse to a longitudinal axis "A-A" defined by first lever arm 10 and may be in opposite directions. First engaging portion 14 defines an acute angle with respect to longitudinal axis "A-A." Under such a configuration, non-engaging end 4 of rod bender 100 in the first configuration (FIG. 1) defines a gap 4a between first engaging portions 14, 24 of first and second lever arms 10, 20 to facilitate outward manipulation of first engaging portions 14, 24 of first and second lever arms 10, 20. In addition, under such a configuration, non-engaging end 9 of rod bender 100 in the second configuration (FIG. 7) defines a gap 9a between second engaging portion 16 of first lever arm 10 and first engaging portion 24 of second lever arm 20. In addition, elongate body 12 may be tapered toward first and second engaging portions 14, 16.

With reference now to FIGS. 4 and 5, a second lever arm 20 includes an elongated body 22 extending between first and second engaging portions 24, 26. Each of first and second engaging portions 24, 26 defines a notch 24a, 26a dimensioned to receive surgical rod 90 therein. Each of first and second engaging portions 24, 26 further defines an opening 24b, 26b leading into notch 24a, 26a. Openings 24b, 26b may be transverse to a longitudinal axis "B-B" defined by second lever 20. First engaging portion 24 of second lever arm 20 defines an acute angle with respect to longitudinal axis "B-B." Under such a configuration, non-engaging end 4 of rod bender 100 in the first configuration (FIG. 1) defines gap 4a between first engaging portions 14, 24 of first and second lever arms 10, 20 to facilitate outward manipulation of first engaging portions 14, 24 of first and second lever arms 10, 20.

With continued reference to FIGS. 4 and 5, second arm 20 further includes first and second hinge portions 30, 32 adjacent respective first and second engaging portions 24, 26. Each of first and second hinge portions 30, 32 serves as a hinge when rod bender 100 is in the second configuration (FIG. 7). Under such a configuration, as non-engaging end 9 of rod bender 100 is spread apart, engaging end 7 creates the concave bend in surgical rod 90 by causing first lever arm 10 to hinge against second hinge portion 32 of second lever arm 20. Under such a configuration, rod bender 100 may create a bend in surgical rod 90 that is, e.g., 90 degrees or more. Furthermore, first and second hinge portions 30, 32 include opposing first and second guide portions 30a, 32a, respectively. First and second guide portions 30a, 32a are dimensioned such that first lever arm 10 is received between respective first and second guide portions 30a, 32a and elongate body 22 to provide stability when first lever arm 10 is hinged against first or second hinge portions 30, 32. Under such a configuration, rod bender 100 may create a bend in surgical rod 90 that is, e.g., 90 degrees or more.

Figure 6:
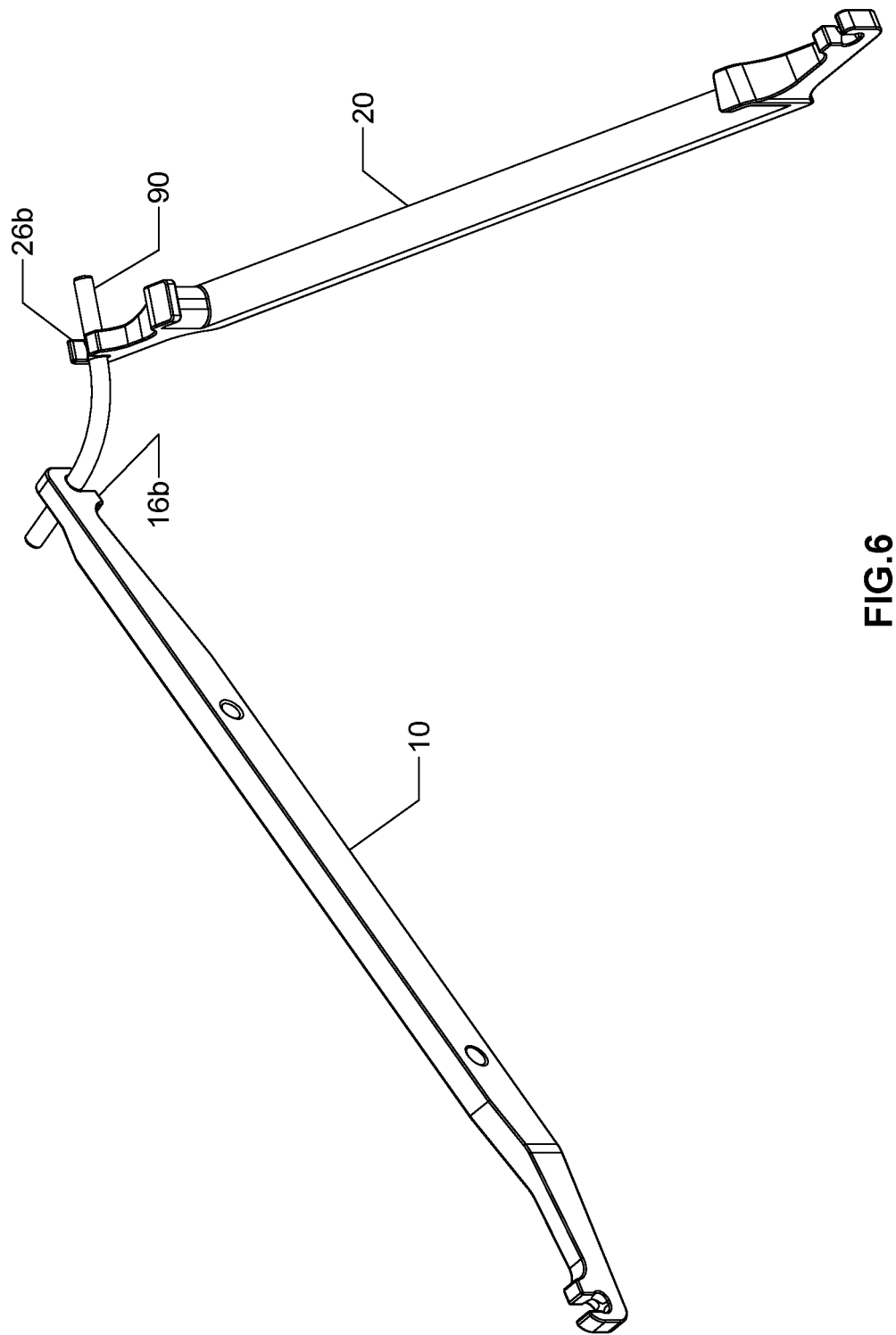
FIG. 6 is a perspective view of the rod bender of FIG. 1 illustrating use in the first configuration.

In use, first and second lever arms 10, 20 may be selectively mated for a desired contour of surgical rod 90. For example, rod bender 100 may be placed in the first configuration in which second engaging portion 16, 26 of first and second lever arms 10, 20 engage surgical rod 90 to create a convex bend in surgical rod 90 (FIG. 1). Under such a configuration, rod bender 100 may create a bend in surgical rod 90 that is, e.g., 90 degrees or more. Initially, surgical rod 90 is positioned within notches 16a, 26a of respective second engaging portions 16, 26 of first and second lever arms 10, 20. This can be done prior to surgical rod 90 being placed within the patient or in-situ. At this time, second engaging portions 16, 26 may be in, e.g., planar contact, with each other. In order to provide stability during bending of surgical rod 90, first and second lever arms 10, 20 may be positioned such that openings 16b, 26b of second engaging portions 16, 26 are in opposite directions. First engaging portions 14, 24 of first and second lever arms 10, 20 (i.e., non-engaging end 4) define a gap 4a therebetween. At this time, first engaging portions 14, 24 of first and second lever arms 10, 20 may be further spread apart in an outward direction as shown by arrows "O" to effect desired bending of surgical rod 90. Surgical rod 90 may be bent further, while second engaging portions 16, 26 of first and second lever arms 10, 20 are spaced apart (FIG. 6) to achieve the desired contour of surgical rod 90.

Figure 8:
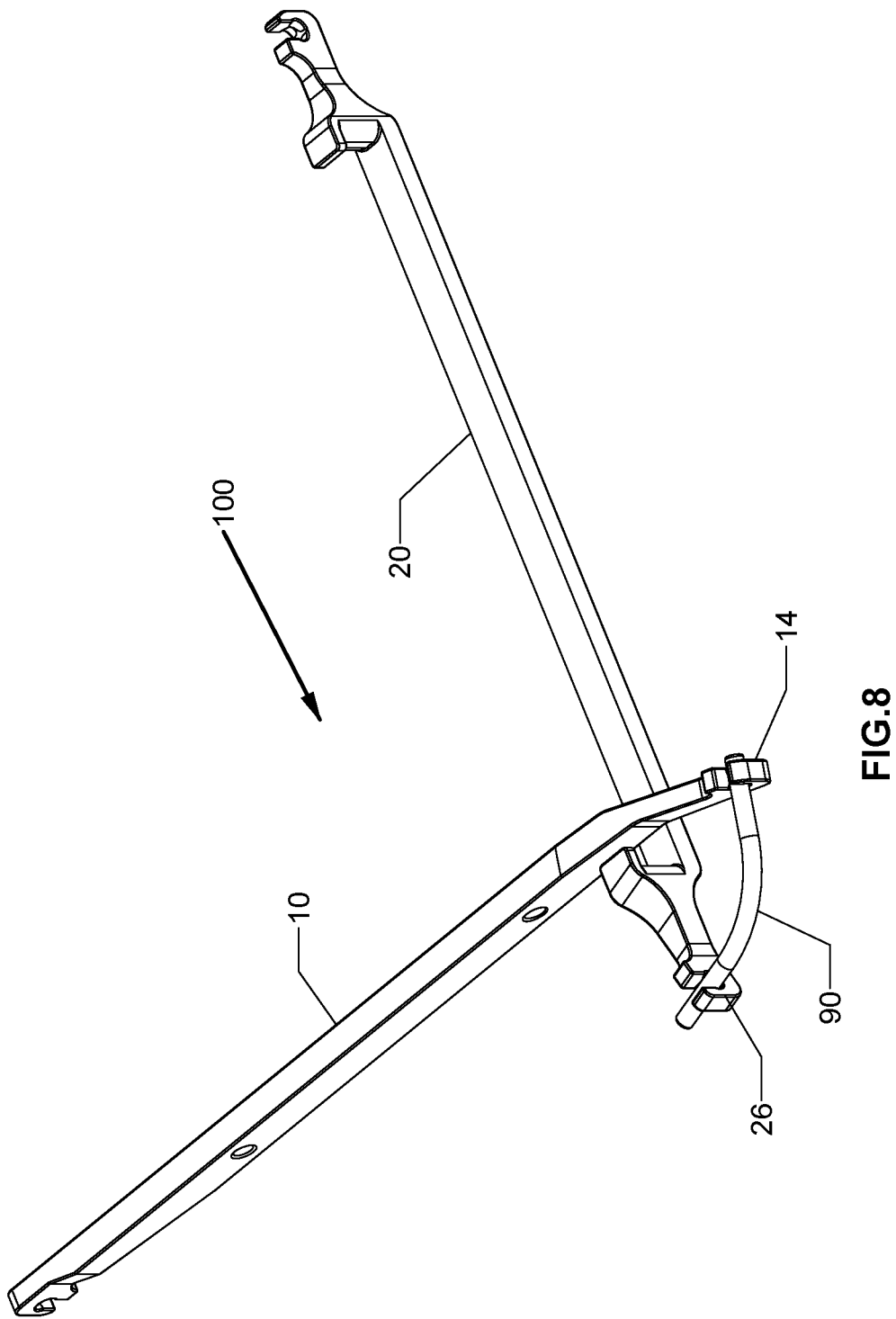
FIG. 8 is a perspective view of the rod bender of FIG. 7 illustrating use in the second configuration.

With reference now to FIGS. 7 and 8, rod bender 100 may be placed in the second configuration to create a concave bend in surgical rod 90. Initially, surgical rod 90 is positioned within notch 14a of first engaging portion 14 of first lever arm 10 and notch 26a of second engaging portion 26 of second lever arm 20. At this time, first engaging portion 14 of first lever arm 10 and second engaging portion 26 of second lever arm 20 may be in, e.g., planar contact, with each other. Meanwhile, second engaging portion 16 of first lever arm 10 and first engaging portion 24 of second lever arm 20 (i.e., non-engaging end 9) defines gap 9a therebetween. Second engaging portion 16 of first lever arm 10 and first engaging portion 24 of second lever arm 20 may be further spread apart in an outward direction as shown by arrows "Y" to create a concave bend in surgical rod 90. Surgical rod 90 may be bent further while first engaging portion 14 of first lever arm 10 and second engaging portion 26 of second lever arm 20 are spaced apart (FIG. 8) to achieve the desired contour of surgical rod 90. It is envisioned that under such a configuration, rod bender 100 in the first and second configurations may create a bend in surgical rod 90 that is, e.g., 90 degrees or more. It is further envisioned that rod bender 100 in the first and second configurations may create a bend in surgical rod that is, e.g., less than 90 degrees.

Although the illustrative embodiments of the present disclosure have been described herein with reference to the accompanying drawings, the above description, disclosure, and figures should not be construed as limiting, but merely as exemplifications of particular embodiments. For example, while the first and second configurations of rod bender 100 is illustrated to create convex and concave bends in surgical rod 90, it is also contemplated second engaging portions 16, 26 of first and second lever arms 10, 20 may engage surgical rod 90 to create the desired bend in surgical rod 90. It is to be understood, therefore, that the disclosure is not limited to those precise embodiments, and that various other changes and modifications may be effected therein by one skilled in the art without departing from the scope or spirit of the disclosure.

What is claimed is:

1. A rod bender comprising:
   a first arm defining a longitudinal axis, the first arm including first and second engaging portions configured to engage a surgical rod, at least one of the first or second engaging portions defining an acute angle with respect to the longitudinal axis;
   a second arm including third and fourth engaging portions configured to engage the surgical rod, and a hinge portion adjacent the third or fourth engaging portions, wherein the rod bender is reconfigurable between a first configuration in which the second and fourth engaging portions of the first and second arms engage the surgical rod such that spreading of the first and third engaging portions of the first and second arms bends the surgical rod in a first-orientation, and a second configuration in which the first engaging portion of the first arm and the fourth engaging portion of the second arm engage the surgical rod and a portion of the first arm contacts the hinge portion of the second arm such that spreading of the second engaging portion of the first arm and the third engaging portion of the second arm bends the surgical rod in a second orientation opposite to the first orientation,
   wherein, in the second configuration, the portion of the first arm is at least partially received within the hinge portion of the second arm.

2. The rod bender according to claim 1, wherein each engaging portion of the first and second engaging portions of the first arm defines a notch configured to receive the surgical rod and an opening leading into the notch.

3. The rod bender according to claim 2, wherein the openings of the first and second engaging portions of the first arm are transverse to the longitudinal axis of the first arm.

4. The rod bender according to claim 2, wherein the openings of the first and second engaging portions of the first arm are defined in opposite directions.

5. The rod bender according to claim 1, wherein at least one of the third or fourth engaging portions of the second arm defines an acute angle with respect to a longitudinal axis defined by the second arm.

6. The rod bender according to claim 5, wherein the third engaging portion of the second arm defines the acute angle with respect to the longitudinal axis of the second arm.

7. The rod bender according to claim 6, wherein the first engaging portion of the first arm defines the acute angle with respect to the longitudinal axis of the first arm.

8. The rod bender according to claim 5, wherein the second arm includes an elongate body extending between the third and fourth engaging portions of the second arm, the elongate body aligned with the longitudinal axis of the second arm.

9. The rod bender according to claim 1, wherein the hinge portion of the second arm includes a guide portion configured to provide stability when the portion of the first arm is hinged against the hinge portion of the second arm.

10. The rod bender according to claim 1, wherein the hinge portion is adjacent the fourth engaging portion of the second arm.

11. A rod bender for bending a surgical rod comprising:
    a first arm including opposing first and second ends; and
    a second arm including opposing third and fourth ends and a hinge portion, the rod bender selectively configurable between a first configuration in which the second and fourth ends of the first and second arms engage the surgical rod for bending the surgical rod in a first orientation and a second configuration in which the first end of the first arm and the fourth end of the second arm engage the surgical rod and the first arm contacts the hinge portion of the second arm for bending the surgical rod in a second orientation opposite to the first orientation, wherein, in the second configuration, the portion of the first arm is at least partially received within the hinge portion of the second arm.

12. The rod bender according to claim 11, wherein at least one end of the first or second ends of the first arm defines a notch configured to receive the surgical rod and an opening leading into the notch.

13. The rod bender according to claim 12, wherein the opening of the at least one end of the first or second ends of the first arm is transverse to a longitudinal axis of the first arm.

14. The rod bender according to claim 11, wherein at least one end of the third or fourth ends of the second arm defines a notch configured to receive the surgical rod and an opening leading into the notch.

15. The rod bender according to claim 11, wherein at least one of the third or fourth ends of the second arm defines an acute angle with respect to a longitudinal axis defined by the second arm.

16. The rod bender according to claim 15, wherein the third end of the second arm defines the acute angle with respect to the longitudinal axis of the second arm.

17. The rod bender according to claim 16, wherein the first end of the first arm defines the acute angle with respect to a longitudinal axis of the first arm.

18. The rod bender according to claim 11, wherein the surgical rod in the first orientation defines a convex profile.

19. The rod bender according to claim 11, wherein the surgical rod in the second orientation defines a concave profile.

20. A method of surgery comprising:
providing a rod bender including:
a first arm including first and second engaging portions configured to engage a surgical rod, the first engaging portion offset from a longitudinal axis defined by the first arm; and
a second arm including third and fourth engaging portions configured to engage a surgical rod;
securing a surgical rod with the second and fourth engaging portions or the first and fourth engaging portions of the respective first and second arms; and
bending the surgical rod by, in a first configuration, spreading the first and third engaging portions bends the surgical rod in a first orientation, or, in a second configuration, spreading the second and third engaging portions of the respective first and second arms by engaging a portion of the first arm with a hinge portion of the second arm bends the surgical rod in a second orientation opposite to the first orientation, wherein, in the second configuration, the portion of the first arm is at least partially received within the hinge portion of the second arm.

21. The method according to claim 20, wherein securing the surgical rod includes engaging the surgical rod with the second engaging portion of the first arm and the fourth engaging portion of the second arms such that spreading of the first engaging portion of the first arm and the third engaging portion of the second arm bends the surgical rod in a convex profile.

22. The method according to claim 21, wherein securing the surgical rod includes engaging the surgical rod with the first engaging portion of the first arm and the fourth engaging portion of the second arm such that spreading of the second engaging portion of the first arm and the third engaging portion of the second arm bends the surgical rod in a concave profile.

* * * * *